(12) United States Patent
Cha

(10) Patent No.: US 8,322,043 B2
(45) Date of Patent: Dec. 4, 2012

(54) AUTOMATIC ANTHROPOMETER

(75) Inventor: Ki Chul Cha, Seoul (KR)

(73) Assignee: Biospace Co., Ltd., Seoul (KR)

( * ) Notice: Subject to any disclaimer, the term of this patent is extended or adjusted under 35 U.S.C. 154(b) by 78 days.

(21) Appl. No.: 12/964,167

(22) Filed: Dec. 9, 2010

(65) Prior Publication Data

US 2011/0167658 A1 Jul. 14, 2011

(30) Foreign Application Priority Data

Jan. 12, 2010 (KR) .................... 20-2010-0000302 U
Jan. 12, 2010 (KR) .................... 20-2010-0000303 U

(51) Int. Cl.
G01B 5/02 (2006.01)
G01B 7/02 (2006.01)

(52) U.S. Cl. ............................. 33/832; 33/515
(58) Field of Classification Search ............. 33/832, 33/512, 515
See application file for complete search history.

(56) References Cited

U.S. PATENT DOCUMENTS

| 1,001,814 | A | * | 8/1911 | Carr | 33/512 |
| 1,371,281 | A | * | 3/1921 | Weber | 33/512 |
| 1,860,184 | A | * | 5/1932 | Jacobs | 33/512 |
| 3,196,551 | A | * | 7/1965 | Provost et al. | 33/515 |
| 4,134,213 | A | * | 1/1979 | Kushmuk | 33/512 |
| 6,003,235 | A | * | 12/1999 | Chen | 33/512 |
| 6,401,352 | B1 | * | 6/2002 | Kimura et al. | 33/832 |
| 6,446,351 | B1 | * | 9/2002 | Zhang et al. | 33/832 |
| 6,745,488 | B2 | * | 6/2004 | Jordil et al. | 33/832 |
| 6,919,517 | B2 | * | 7/2005 | Montagnino et al. | 177/171 |
| 7,200,952 | B2 | * | 4/2007 | Montagnino | 33/832 |
| 8,006,400 | B2 | * | 8/2011 | Gerster | 33/512 |
| 2006/0137204 | A1 | * | 6/2006 | Yang | 33/832 |

FOREIGN PATENT DOCUMENTS

JP 61-154906 9/1986
JP 06-022939 2/1994

* cited by examiner

Primary Examiner — Christopher Fulton
(74) Attorney, Agent, or Firm — Gilberto M. Villacorta; Jessica A. Flores; Foley & Lardner LLP

(57) ABSTRACT

An automatic anthropometer for automatically measuring human height is provided. The automatic anthropometer includes a main post configured to stand vertically to a foot board and have a guiding rail formed integrally with an inner surface in a length direction, a sliding post configured to include a guide wheel that rotates along the guiding rail, and ascend and descend along the length direction of the main post under the guide of the guiding rail to measure height of a user, a head-touch bar configured to be coupled to the sliding post, and a lifting-driving device configured to raise and lower the sliding post.

5 Claims, 6 Drawing Sheets

AUTOMATIC ANTHROPOMETER

CROSS-REFERENCE TO RELATED APPLICATION(S)

This application claims the benefit under 35 U.S.C. §119 (a) of Korean Utility Application Nos. 20-2010-0000302, filed on Jan. 12, 2010, and 20-2010-0000303, filed on Jan. 12, 2010, in the Korean Intellectual Property Office, the entire disclosures of which are incorporated herein by references for all purposes.

BACKGROUND

1. Field

The following description relates to an automatic anthropometer for measuring human height.

2. Description of the Related Art

Human height is the distance from the bottom of the feet to the top of the head in a human body standing erect, and it is regarded as a representative measurement showing the length of a body or the status of the growth and development of the body. For measuring height, a manual or an automatic anthropometer is used. A general automatic anthropometer measures height of a user using a head-touch bar that descends along a vertical post by driving a motor until it touches the head of the user. When the head-touch bar touches the head of the user, an electrical signal is output from a contact detection sensor embedded in the head-touch bar, and at the time of outputting the electrical signal, the height of the user is measured and displayed based on current position information of the head-touch bar.

However, the above described general automatic anthropometer includes a vertical post which is assembled by an exterior case and a guiding rail for guiding a head-touch bar in the exterior case, and thus it is rather complicated in structure. Thus, such complicated structure may be difficult in terms of maintenance.

Moreover, when the head-touch bar is ascending and descending along the vertical post, the vertical post guides the head-touch bar, preventing it from being slid off of the post. For example, if the maximum measurable height of the automatic anthropometer is 2000 mm, the vertical post must be longer than 2000 mm and must fixedly stand vertically to a foot board, and the head-touch bar ascends up to the height of 2000 mm without sliding off the top of the post.

In this case, since the vertical post is fixed to stand vertically to the base, having a length greater than the maximum measurable height, it occupies a large space for storage, and is inconvenient to move. Furthermore, in the case of moving the automatic anthropometer for mobile medical services in, for example, government and public offices and schools, it may be difficult to carry the automatic anthropometer by a vehicle due to its length.

SUMMARY

The following description relates to an automatic anthropometer which includes a simple structure for guiding and facilitating ascending and descending movements of a head-touch bar which allows easy maintenance. In addition, the following description relates to an automatic anthropometer that requires a small space for storage and is easy to carry when it is needed for such services as mobile medical services.

In one general aspect, there is provided an automatic anthropometer including: a main post configured to stand vertically to a foot board and have a guiding rail formed integrally with an inner surface in a length direction; a sliding post configured to include a guide wheel that rotates along the guiding rail, and ascend and descend along the length direction of the main post under the guide of the guiding rail to measure height of a user; a head-touch bar configured to be coupled to the sliding post; and a lifting-driving device configured to raise and lower the sliding post.

In another general aspect, there is provided an automatic anthropometer including: a main post configured to stand vertically to a foot board; a sliding post configured to measure height of a user while ascending and descending between a highest position and a lowest position along a length direction of the main post, and to overlap the main post when descending to the lowest position and protrude above the main post when ascending to the highest position; a head-touch bar configured to be coupled to the sliding post; and a lifting-driving device configured to raise and lower the sliding post.

Other features and aspects will be apparent from the following detailed description, the drawings, and the claims.

Figure 1:
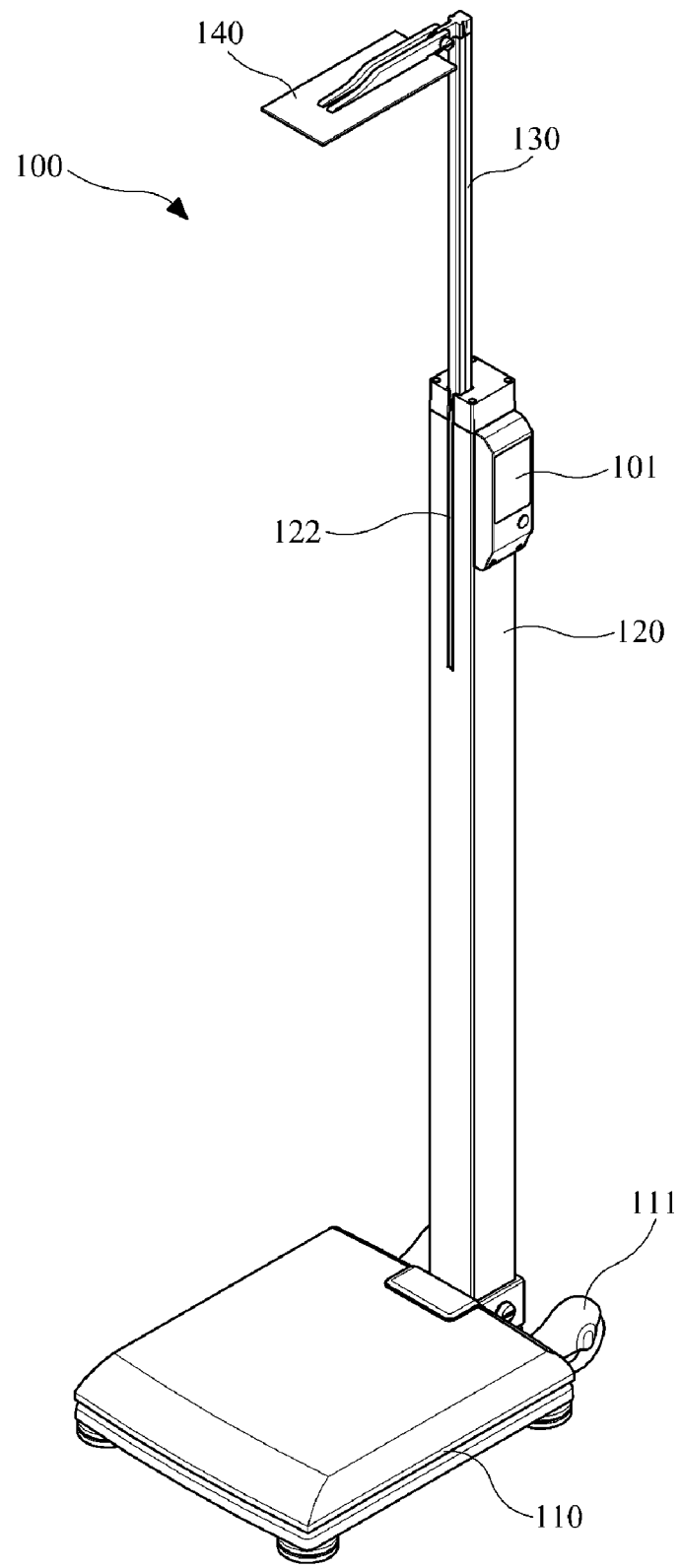
FIG. 1 is a diagram showing a perspective view of an example of an automatic anthropometer.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Figure 2:
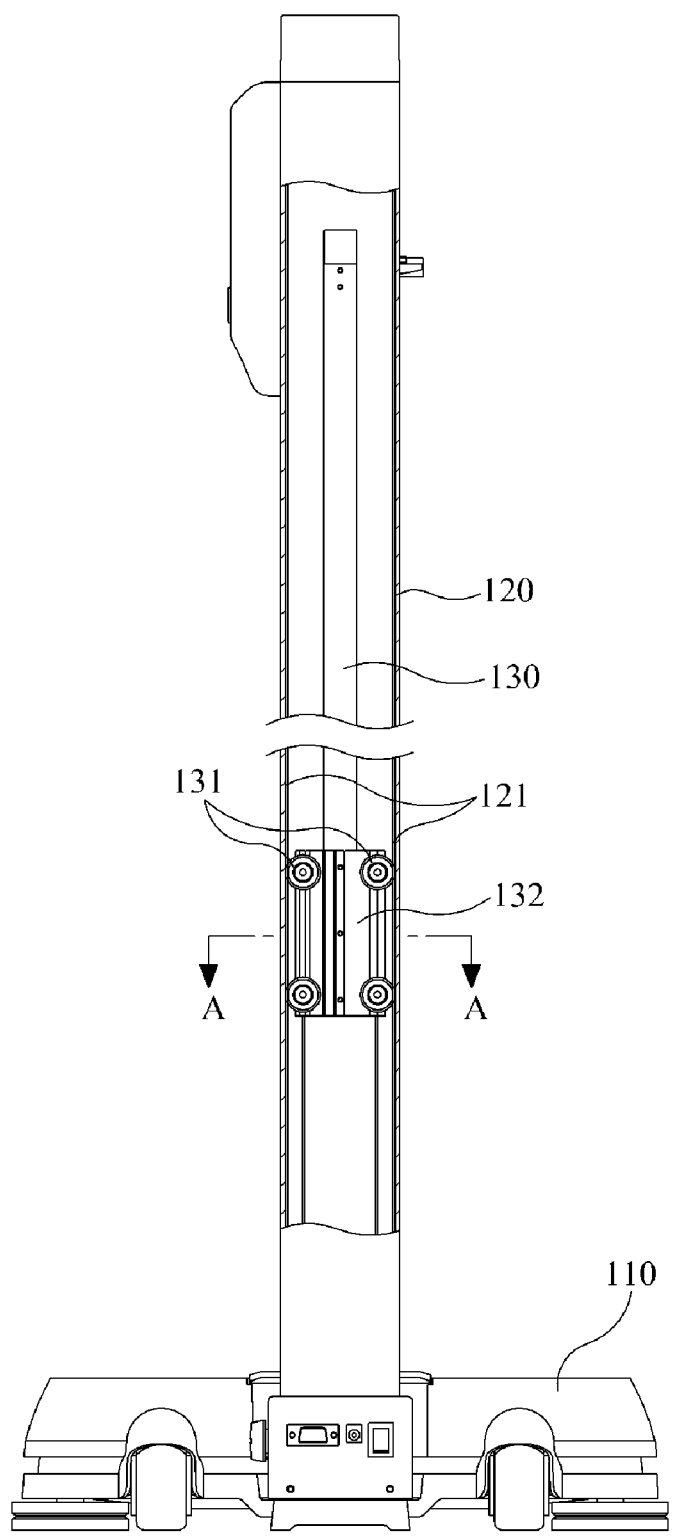
FIG. 2 is a diagram showing a vertical cross-sectional view of a main post of the automatic anthropometer shown in the example illustrated in FIG. 1.
Figure 3:
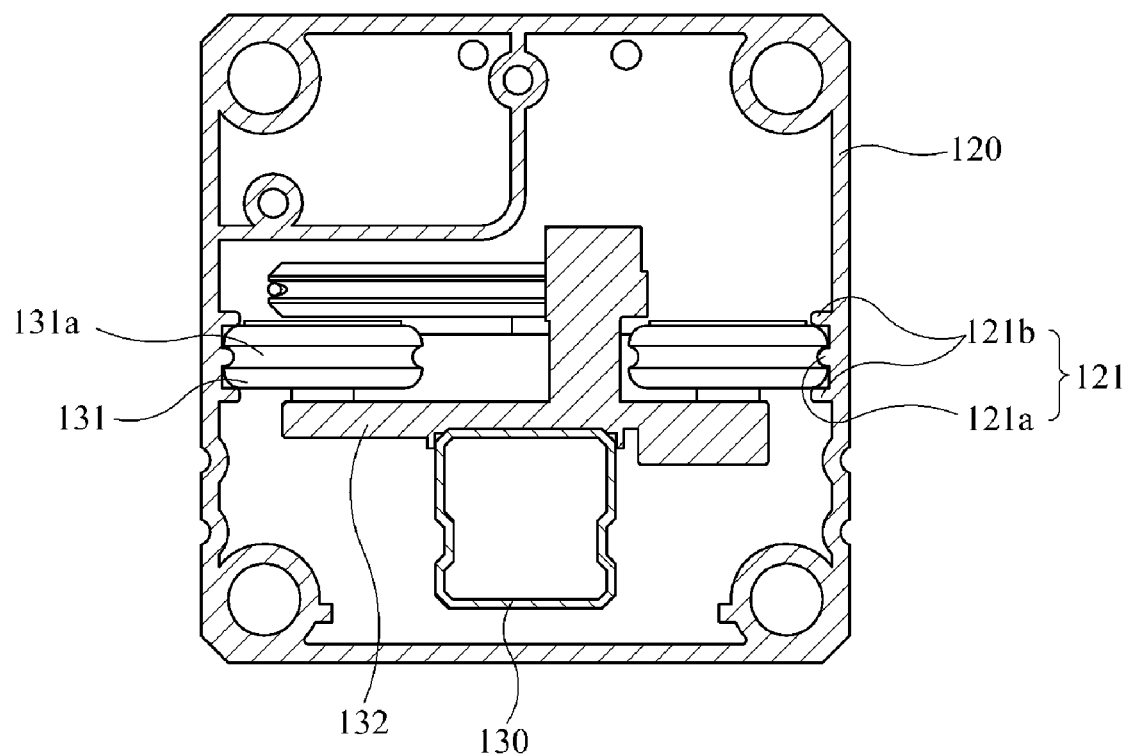
FIG. 3 is a diagram showing a horizontal cross-sectional view taken along line A-A of FIG. 2.

FIG. 1 illustrates a diagram showing a perspective view of an example of an automatic anthropometer, and FIG. 2 illustrates a diagram showing a vertical cross-sectional view of a main post of the automatic anthropometer shown in the example illustrated in FIG. 1. FIG. 3 illustrates a diagram showing a horizontal cross-sectional view taken along line A-A of FIG. 2.

Figure 4:
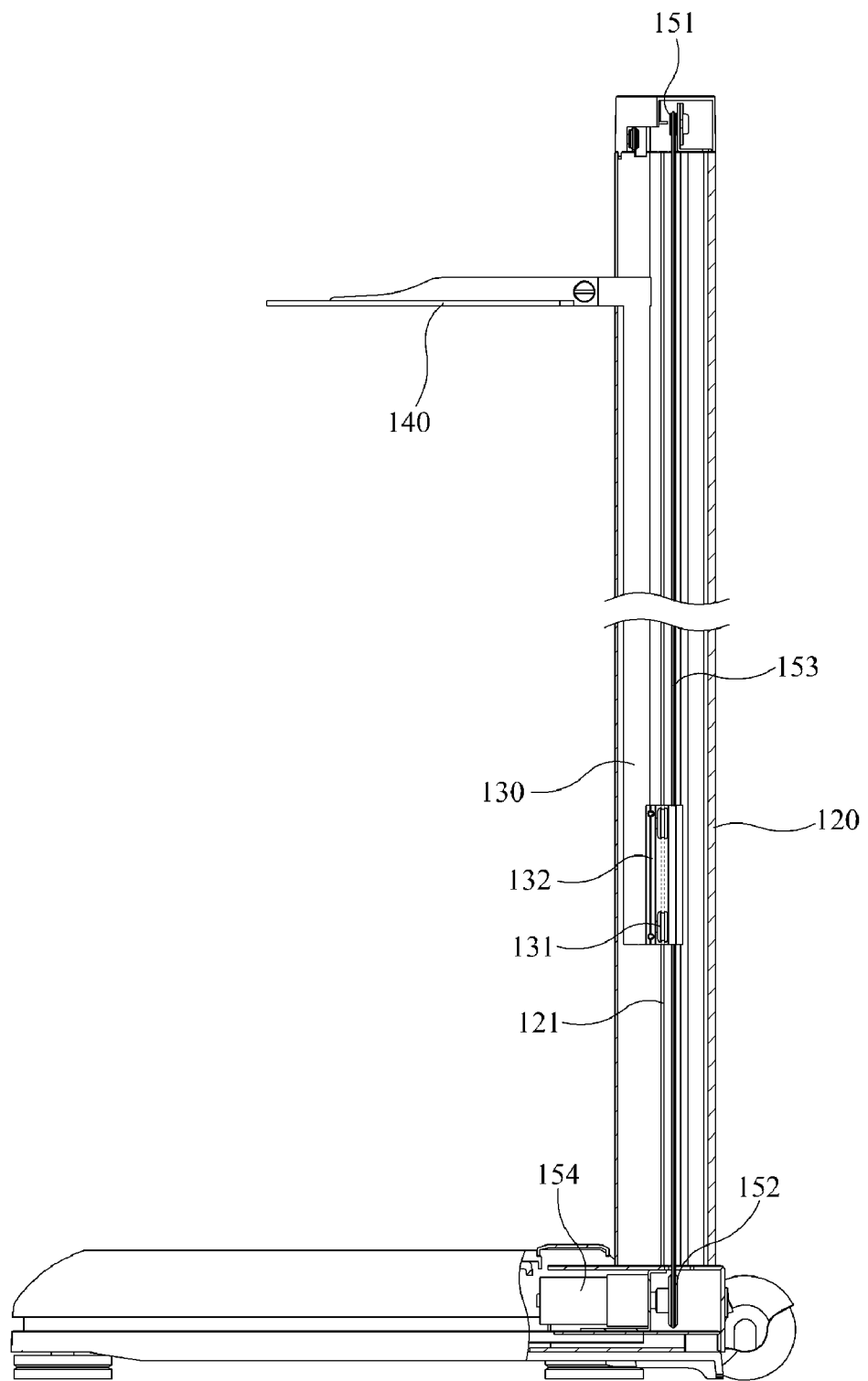
FIG. 4 is a diagram showing a vertical cross-sectional view of an example of a lifting-driving device shown in the example illustrated in FIG. 1.
Figure 5:
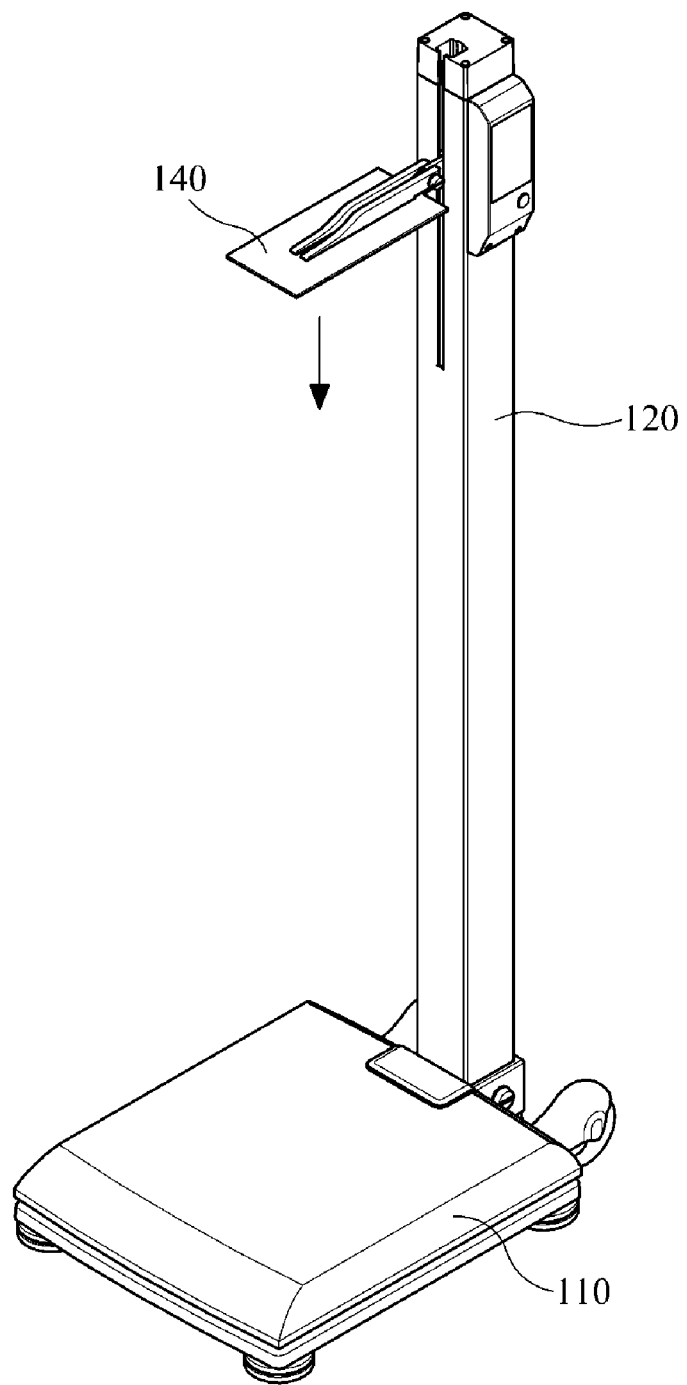
FIG. 5 is a diagram showing a perspective view of an example of a sliding post descending in the example illustrated in FIG. 1.

Referring to the examples illustrated in FIGS. 1 to 3, the automatic anthropometer 100 may include a foot board 110, a main post 120, a sliding post 130, a head-touch bar 140, and a lifting-driving device (see FIG. 4).

The foot board 110 may be configured to allow a user to stand to measure height of the user. The main post 120 is coupled with the foot board 110 while standing vertically from the foot board 110. The sliding post 130 may ascend together with the head-touch bar 140 along a length of the main post 120, allowing the measurement of height of the user. The head-touch bar 140 may be coupled with the sliding post 130. In addition, the lifting-driving device may raise and lower the sliding post 130.

The main post 120 may include a guiding rail 121 integrally formed inside so as to guide ascending and descending movements of the sliding post 130 to which the head-touch bar 140 is coupled, as shown in FIG. 2. The guiding rail 121 may extend along a direction of ascent and descent of the sliding post 130, that is, a length direction of the main post 120. Then, the sliding post 130 may include a guide wheel 131. The guide wheel 131 rotates along the guiding rail 121, thereby facilitating the ascending and descending movements of the sliding post 130 under the guide of the guiding rail 121. The guide wheel 131 may be rotatably installed on a sliding bracket 132 (see FIG. 4) coupled to a lower portion of the sliding post 130.

The guiding rail 121 may be formed as a pair of rails which are disposed, respectively, on inner walls of the main post 120 that face each other. In this case, at least one guide wheel 131 may be provided to each of the paired rails of the guiding rail 121. Accordingly, the ascending and descending movements of the sliding post 130 may be guided by the guiding rails 121 and the guide wheels 131 on both sides of the sliding post 130, and thus more stable movements of the sliding post 130 can be realized. If numerous guide wheels 131 are vertically disposed on each of the guiding rails 121 as shown in the example illustrated in FIG. 2, the sliding post 130 may be guided more stably and smoothly.

As shown in the example illustrated in FIG. 3, each of the guide wheels 131 may include a groove 131*a* formed along the center of a circumference thereof. In this case, each of the guiding rails 121 may include a center projection portion 121*a* and a pair of edge projection portions 121*b*. The center projection portion 121*a* protrudes from the inner wall of the main post 120 toward the groove 131*a* of the guide wheel 131 and extends in the length direction of the main post 120, thereby guiding rotation of the guide wheel 131. The edge projection portions 121*b* protrude from the inner wall of the main post 120 toward both sides of the guide wheel 131 and extend in the length direction of the main post, thereby guiding the rotation of the guide wheel 131.

As described above, the guiding rails 121 are not assembled with the main post 120 as additional means, but are formed integrally with the inner walls of the main post 120. Consequently, the inner structure of the main post 120 can be simplified, and thus its maintenance can be easily carried out. In addition, since the guiding rails 121 do not need to be assembled with the main post 120, defect that may occur during the assembly process can be prevented.

Moreover, since the sliding post 130 ascends and descends along the guiding rails 121 by means of the guide wheels 131, the sliding post 130 may more stably ascend and descend with less friction and abrasion thereon, compared to when the sliding post 130 ascends and descends along the guiding rails 121 in direct contact with the guiding rails 121.

The above-described head-touch bar 140 may be disposed to allow the head of the user and the surface contacting the head to be horizontal to each other. Here, the head-touch bar 140 may be coupled to an upper end of the sliding post 130.

When the head-touch bar 140 descends until it touches the head of the user and no longer moves, an encoder value that counts the number of rotations of a rotational motor 154 on the lifting-driving device which will be described later is not changed. Based on the encoder value at this moment, a control unit may calculate height of the user and display it on a display unit 101 (see FIG. 1).

As another example, the head-touch bar 140 may include a contact detection sensor. The contact detection sensor may output an electrical signal when the head-touch bar 140 descends and touches the head of the user. The electrical signal output from the contact detection sensor may be input to the control unit. The control unit may calculate the height of the user based on location information of the head-touch bar 140 at the time of outputting the electrical signal from the contact detection sensor, and display the calculation result to the display unit 101. The location of the head-touch bar 140 may be detected by a position sensor installed on the main post 120, or the above-described encoder.

Referring to an example illustrated in FIG. 4, the lifting-driving device may include an upper pulley 151, a lower pulley 152, a wire 153, and a rotational motor 154. The upper pulley 151 may be installed rotatably on an upper portion of the main post 120, and the lower pulley 152 may also be installed rotatably on a lower portion.

The wire 153 may be provided from the upper pulley 151 to the lower pulley 152, and be coupled to the lower portion of the sliding post 130, for example, a sliding bracket 132. The rotational motor 154 may rotate the lower pulley 152 forward and backward. The lower pulley 152 rotated forward and backward by the rotational motor 154 may allow the wire 153 to move forward and backward, thereby enabling the sliding post 130 to ascend and descend.

The sliding post 130 may ascend to the highest position and protrude above the main post 120 as shown in the example illustrated in FIG. 1, and may descend to the lowest position and fully overlap the main post 120 at the lowest position. In this regard, the main post 120 may have such a length that allows the sliding post 130 to overlap the main post 120 at the lowest position and to protrude above the main post 120 at the highest position. In this case, the lowest position may correspond to a minimum height to be measured and the highest position may correspond to a maximum height to be measured.

For example, if the maximum measurable height is 2000 mm, a length from a bottom of the foot board 110 to the upper end of the main post 120 may be defined as about 1350 mm. In addition, if the minimum measurable height is 900 mm, the main post 120 may include a guide groove 122 (see FIG. 1) on one side so that the head-touch bar 140 can descend to a position 900 mm above a top surface of the foot board 110.

The above structure enables the sliding post 130 to protrude above the main post 120 at the highest position, and thus the length of the main post 120 can be reduced to about half of the maximum measurable height value. Thus, when the automatic anthropometer 100 is not in use, the sliding post 130 may descend to the lowest position to overlap the main post 120, and hence it can be compact.

Accordingly, the automatic anthropometer 100 may require less storage space, and the user can easily carry the automatic anthropometer 100. Furthermore, the automatic anthropometer 100 can be easily carried in a small vehicle, for example, a trunk of a car, when it is needed for mobile medical services in government and public offices and schools.

Figure 6:
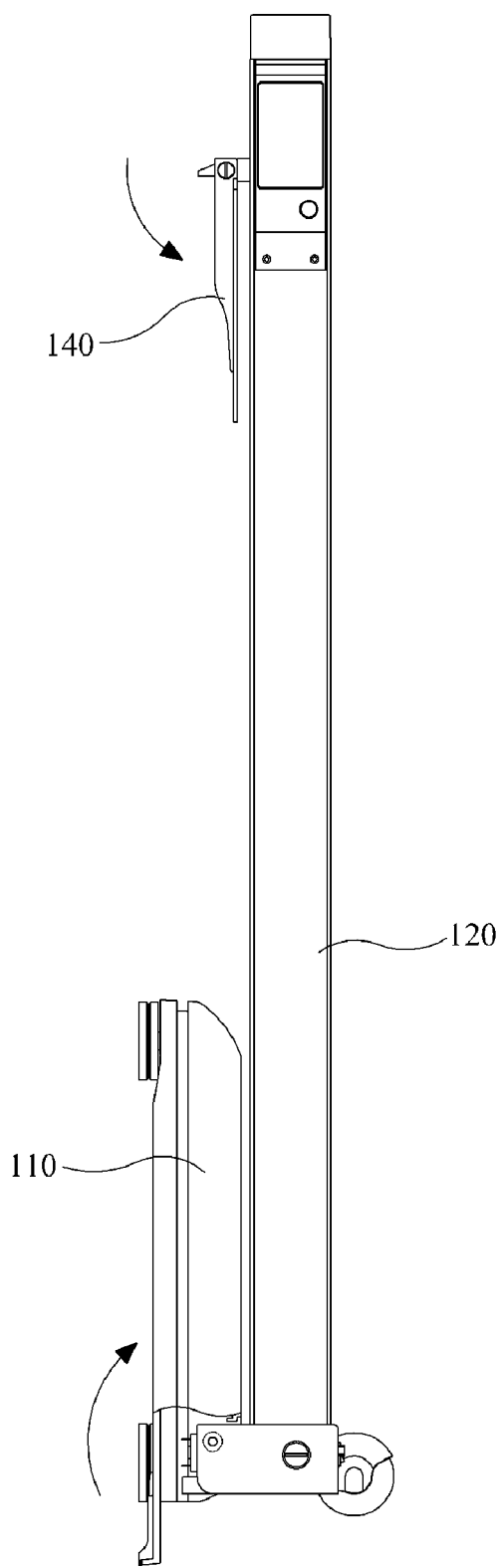
FIG. 6 is a diagram showing a side view of an example of the automatic anthropometer having its foot board folded over a main post and its head-touch bar folded over the sliding post.

The main post 120 may be foldably coupled to the foot board 110 by a hinge while the main post 120 is in a position of standing vertically to the foot board 110 as shown in an example illustrated in FIG. 6. If the main post 120 is folded over the foot board 110, the automatic anthropometer 100 may become more compact. Thus, it is easier to store and carry the automatic anthropometer 100.

The main post 120 may be fixed on the foot board 110, standing erect or being folded over the foot board 110. To this end, a screw groove may be formed in an inner side of an axis hole on each of the foot board 110 and the main post 120, and a bolt functioning as a hinge axis as well may be coupled to the screw groove of the axis hole. The user may secure or release the main post 120 by tightening or loosening the bolt.

Moreover, the head-touch bar 140 may be foldably coupled to the sliding post 130 by a hinge while the head-touch bar 140 is in a position perpendicular to the sliding post 130 and horizontal to the ground. When the head-touch bar 140 is folded over the sliding post 130, the automatic anthropometer 100 can become more compact. Accordingly, it can be easier to store and carry the automatic anthropometer 100.

The head-touch bar 140 may be fixed to the sliding post 130, being in a position perpendicular to the sliding post 130 or being folded over the sliding post 130. To this end, a screw groove may be formed on an inner surface of an axis hole formed on each of the head-touch bar 140 and the sliding post 130, and a bolt functioning as a hinge axis may be coupled to the screw groove.

The foot board 110 may further include moving wheels 111. The moving wheels 111 may help the user move the automatic anthropometer 100 easily. The moving wheels 111 may include a pair of wheels. The moving wheels 111 may be provided on a side of the foot board 110 to which the main post 120 is coupled by a hinge. As the result, the user can move the automatic anthropometer 100 with ease by holding the main post 120 while the foot board 110 is folded over the main post 120.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An automatic anthropometer comprising:
    a main post configured to stand vertically to a foot board and have a guiding rail formed integrally with opposing inner walls of the main post in a length direction of the main post;
    a sliding post configured to include a guide wheel that rotates along the guiding rail, and ascend and descend along the length direction of the main post guided by the guiding rail to measure height of a user;
    a head-touch bar configured to be coupled to the sliding post; and
    a lifting-driving device configured to raise and lower the sliding post,
    wherein the guide wheel includes a groove formed along a center of a circumference of the guide wheel,
    the guiding rail includes a center projection portion and a pair of edge projection portions,
    the center projection portion protrudes from each of the opposing inner walls of the main post toward the groove of the guide wheel and extends in the length direction of the main post, thereby guiding rotation of the guide wheel, and
    the edge projection portions protrude from each of the opposing inner walls of the main post toward the guide wheel and extend in the length direction of the main post, thereby guiding the rotation of the guide wheel, each edge projection portion interfacing with a side of the guide wheel.

2. The automatic anthropometer of claim 1, wherein the main post includes a guide groove on one side so that the head-touch bar coupled to the sliding post can descend along the length direction of the main post, and
    the sliding post is further configured to overlap the main post so that the head-touch bar can descend into the main post through the guide groove of the main post at a lowest position and ascend to protrude above the main post at a highest position.

3. The automatic anthropometer of claim 2, wherein the head-touch bar is configured to be coupled to the sliding post by a hinge so that the head-touch bar can be folded over the sliding post.

4. The automatic anthropometer of claim 2, wherein the main post is further configured to be coupled to the foot board by a hinge so that the main post can be folded with respect to the foot board.

5. The automatic anthropometer of claim 2, wherein the foot board is configured to include a moving wheel.

* * * * *